(12) United States Patent
Thiberville et al.

(10) Patent No.: US 8,923,955 B2
(45) Date of Patent: Dec. 30, 2014

(54) USE OF A SYSTEM FOR IMAGING BY FIBER-OPTIC CONFOCAL FLUORESCENCE IN VIVO IN SITU, SYSTEM AND METHOD FOR IMAGING BY FIBER-OPTIC CONFOCAL FLUORESCENCE IN VIVO IN SITU

(75) Inventors: Luc Thiberville, Notre Dame De Bondeville (FR); Charlotte Cave, Paris (FR); Véronique Dentan, Paris (FR); Nicolas Boularot, Le Perreux sur Marne (FR); Geneviève Bourg-Heckly, Paris (FR); Eric Peltier, Clamart (FR)

(73) Assignees: Mauna Kea Technologies, Paris (FR); Universite de Rouen, Mont Saint Aignan (FR)

( * ) Notice: Subject to any disclaimer, the term of this patent is extended or adjusted under 35 U.S.C. 154(b) by 1216 days.

(21) Appl. No.: 12/377,819

(22) PCT Filed: Aug. 16, 2007
(Under 37 CFR 1.47)

(86) PCT No.: PCT/FR2007/001371
§ 371 (c)(1),
(2), (4) Date: Sep. 29, 2010

(87) PCT Pub. No.: WO2008/020130
PCT Pub. Date: Feb. 21, 2008

(65) Prior Publication Data
US 2012/0035484 A1    Feb. 9, 2012

(30) Foreign Application Priority Data
Aug. 17, 2006 (FR) ...................... 06 07344

(51) Int. Cl.
A61B 6/00 (2006.01)
A61B 1/267 (2006.01)
A61B 1/04 (2006.01)
A61B 1/273 (2006.01)
A61B 5/00 (2006.01)
A61B 1/00 (2006.01)
A61B 1/018 (2006.01)

(52) U.S. Cl.
CPC ............... *A61B 1/2676* (2013.01); *A61B 1/043* (2013.01); *A61B 1/2736* (2013.01); *A61B 5/0068* (2013.01); *A61B 5/0071* (2013.01); *A61B 5/0084* (2013.01); *A61B 1/00165* (2013.01); *A61B 1/018* (2013.01); *A61B 5/0075* (2013.01)
USPC .......................................... 600/478; 600/476

(58) Field of Classification Search
CPC .... A61B 1/2676; A61B 1/043; A61B 1/2736; A61B 1/00165; A61B 1/018; A61B 5/0068; A61B 5/0071; A61B 5/0084; A61B 5/0075
USPC .................................................. 600/473–480
See application file for complete search history.

(56) References Cited

U.S. PATENT DOCUMENTS 5,590,660 A * 1/1997 MacAulay et al. ............ 600/478
5,784,162 A * 7/1998 Cabib et al. .................. 356/456

(Continued)

*Primary Examiner* — Sanjay Cattungal
(74) *Attorney, Agent, or Firm* — Osha Liang LLP

(57) ABSTRACT

A method for imaging a tissue includes collecting a light signal from at least part of said tissue, using a fiber optic probe for fluorescence imaging, wherein the fiber optic probe comprises a plurality of optic fibers, and wherein a distal tip of the fiber optic probe is placed at a distance from said tissue, said imaging being made confocal at a proximal tip of said fiber optic probe. A fluorescence imaging system includes an endoscope equipped with a working channel, in which a fiber optic probe has been inserted, wherein the fiber optic probe is movable between a retracted position and at least one position of extension, said fiber optic probe comprising a plurality of optic fibers for performing imaging of a tissue, said imaging being confocal via a processor located at a proximal tip of said fiber optic probe.

15 Claims, 4 Drawing Sheets

(56) References Cited

U.S. PATENT DOCUMENTS

| | | | |
|---|---|---|---|
| 5,827,190 A * | 10/1998 | Palcic et al. | 600/476 |
| 5,845,646 A * | 12/1998 | Lemelson | 128/899 |
| 6,174,291 B1 * | 1/2001 | McMahon et al. | 600/564 |
| 6,462,770 B1 * | 10/2002 | Cline et al. | 348/65 |
| 6,485,413 B1 * | 11/2002 | Boppart et al. | 600/160 |
| 6,537,211 B1 * | 3/2003 | Wang et al. | 600/178 |
| 6,571,118 B1 * | 5/2003 | Utzinger et al. | 600/476 |
| 7,004,173 B2 * | 2/2006 | Sparks et al. | 128/898 |
| 7,235,045 B2 * | 6/2007 | Wang et al. | 600/109 |
| 7,848,791 B2 * | 12/2010 | Schmitt et al. | 600/476 |
| 8,046,057 B2 * | 10/2011 | Clarke | 600/478 |
| 8,129,105 B2 * | 3/2012 | Zuckerman | 435/4 |
| 2002/0093563 A1 * | 7/2002 | Cline et al. | 348/65 |
| 2002/0103459 A1 * | 8/2002 | Sparks et al. | 604/164.13 |
| 2003/0055315 A1 * | 3/2003 | Gatto et al. | 600/114 |
| 2003/0191368 A1 * | 10/2003 | Wang et al. | 600/160 |
| 2004/0002700 A1 * | 1/2004 | Ryan et al. | 606/27 |
| 2005/0027199 A1 * | 2/2005 | Clarke | 600/473 |
| 2005/0059894 A1 * | 3/2005 | Zeng et al. | 600/476 |
| 2007/0016130 A1 * | 1/2007 | Leeflang et al. | 604/95.04 |
| 2007/0135803 A1 * | 6/2007 | Belson | 606/1 |
| 2008/0221388 A1 * | 9/2008 | Seibel et al. | 600/109 |
| 2008/0254531 A1 * | 10/2008 | Zuckerman | 435/288.7 |
| 2008/0262308 A1 * | 10/2008 | Prestezog et al. | 600/123 |
| 2009/0275799 A1 * | 11/2009 | Saadat et al. | 600/109 |
| 2010/0113906 A1 * | 5/2010 | Marple et al. | 600/342 |
| 2011/0319759 A1 * | 12/2011 | Liu et al. | 600/439 |
| 2012/0215065 A1 * | 8/2012 | Mukherjee | 600/108 |
| 2014/0058235 A1 * | 2/2014 | Li et al. | 600/345 |

* cited by examiner

FIG. 3
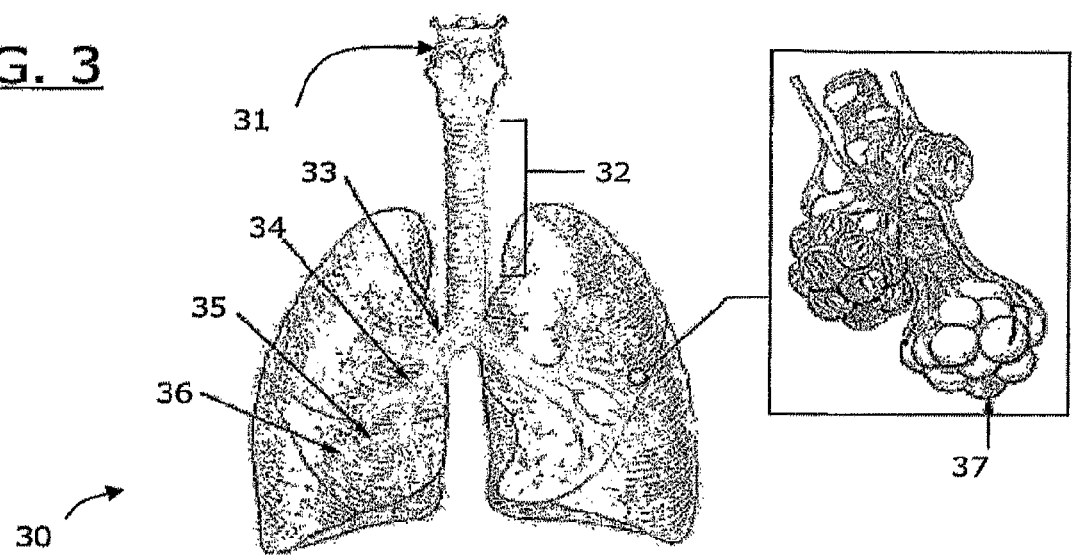
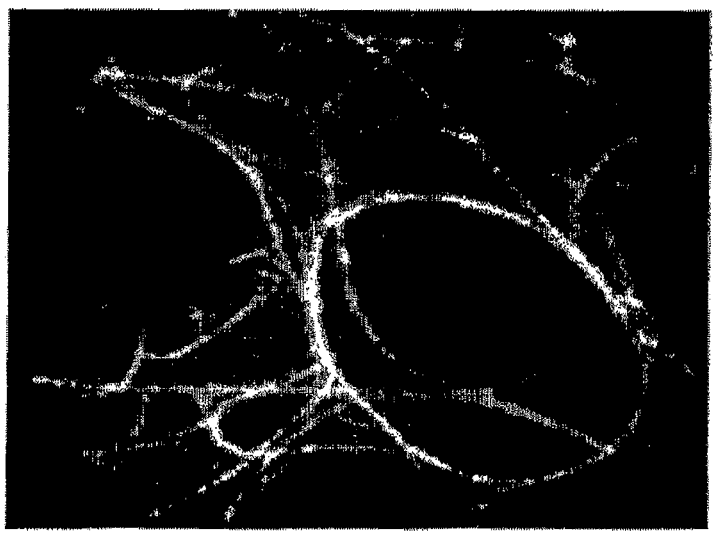
FIG. 4

USE OF A SYSTEM FOR IMAGING BY FIBER-OPTIC CONFOCAL FLUORESCENCE IN VIVO IN SITU, SYSTEM AND METHOD FOR IMAGING BY FIBER-OPTIC CONFOCAL FLUORESCENCE IN VIVO IN SITU

CROSS REFERENCE TO RELATED APPLICATIONS

This is a National Phase Application based on PCT/FR2007/001371.

FIELD OF THE INVENTION

The present invention relates to use of a system for in vivo in situ fiber-optic confocal fluorescence imaging. It also includes a system and method for in vivo in situ fiber-optic confocal fluorescence imaging.

Currently, there exist imaging systems based on fluorescence microscopy using a fiber-optic probe. These systems, initially marketed for use with animals were then applied to clinical research. The first domain of application was in vivo imaging in the domain of gastroenterology. These systems, used in combination with an endoscope, enable a user to obtain microscopic information that complements the macroscopic data supplied by the endoscope.

The clinical application field was then extended to the domain of pneumology. Compared to gastroenterology, this domain of application presents the advantage of previous experience with fluorescence imaging, in particular with auto fluorescence imaging due to the optic properties of the bronchial tree tissue.

However, such in vivo fiber-optic imaging systems, using existing fluorescence, display low resolution. These systems are used for imaging of tissue in vivo in situ using an endoscope with insertion of a fiber optic probe through the working channel of the endoscope and placing of the distal tip of the probe in contact with the tissue under visual control. These systems are thus not used for observing tissues or an alveolus located at a distance that is outside of the direct vision of the endoscope.

At present, other in vivo imaging systems, such as bronchial endoscopes, enable exploration of the bronchial tree up to the fifth-division subsegment. However, these imaging systems do not enable extended visualization beyond that point. The alveoli at the tip of the bronchial tree thus remain inaccessible. Yet, certain pathologies, for example alveolar or interstitial pathologies whether diffuse or focal, as well as peripheral nodules, can only be characterized via anatomical description of the alveolar and bronchioalveolar regions. To obtain visualization of the microarchitecture of these areas, performance of distal pulmonary biopsies of these regions is required via endoscopy or surgery, and these methods are particularly invasive.

SUMMARY OF THE INVENTION

One of the objectives of the invention is to offer a new way of using a fiber optic confocal fluorescence imaging system capable of in vivo in situ observation and imaging of the contents and/or walls of pulmonary alveoli located at a distance from the visual field of bronchial endoscopes.

Another objective of the invention is to offer a fiber optic confocal fluorescence imaging system capable of in vivo in situ imaging of the contents and/or walls of pulmonary alveoli located at a distance from direct endoscopic vision.

Another objective of the invention is to offer a fiber optic confocal fluorescent imaging system capable of in vivo in situ imaging of the contents and/or walls of pulmonary alveoli located at a distance from endoscopic vision.

Embodiments of the invention relate to use of a fiber optic confocal fluorescence imaging system for in vivo in situ imaging. A system in accordance with embodiments of the invention comprises a fiber optic probe for observing the contents and/or walls of pulmonary alveoli located at a distance from the distal tip of an endoscope. A method according to embodiments of the invention enables imaging of tissue or an alveolus located at a distance from the distal tip of an endoscope.

In the present description, an alveolus refers to a pulmonary alveolar system consisting of the respiratory bronchiolus, the alveolar channel, and actual pulmonary alveolar sacs.

In fact, current (conventional) in vivo fiber optic fluorescence imaging systems are used for imaging of tissue with which the distal tip of the fiber optic probe is in contact. These systems are currently used for imaging of tissue with which the probe is in contact, at an axial resolution ranging from 15 to 20 µm. In other words, current systems enable imaging of tissue with which the probe is in contact, at a depth of 0 to 15 µm. Current fiber optic fluorescence imaging systems require that the tip of the probe be in contact with the tissue to be imaged.

However, during in vivo in situ imaging of a pulmonary alveolar system using a fiber optic confocal fluorescence system, it was observed in quite a surprising manner that the images taken enabled observation of tissue and objects located up to 300 µm from the distal tip of the fiber optic probe. This unexpected, and to date unexplained result shows, on the one hand, that it is not necessary to put the distal tip of the probe in contact with all of the tissue to take an image of this tissue, and on the other hand, that there is a possibility to take images of the inside of an alveolus. The distal tip of the probe may be, for example, in contact with tissue located within proximity or in contact with the tissue for which imaging is needed. Similarly, for imaging of an alveolus, the distal tip of the probe may be in contact with tissue within proximity or in contact with the alveolus for which imaging is needed. The tissue in question may, for example, be the wall of an alveolus located within proximity or in contact with the alveolus or tissue for which imaging is needed.

In a method in accordance with an embodiment of the invention, it is possible to image the content and/or the walls of a pulmonary alveolus. Such imaging may otherwise benefit from the autofluoresence properties of lungs, and more particularly of the alveoli. In this case, contrary to usage in the digestive tract, it is not necessary to apply any exogenous chemofluorescents on the tissue to collect a fluorescent signal. Such usage is thus able to benefit from the endogenous chemofluorescents of lungs and alveoli.

According to another aspect of the invention, in vivo fluorescent imaging systems are provided. A system in accordance with embodiments of the invention comprises an endoscope, equipped with a working channel, inside of which a fiber optic probe is inserted. The fiber optic probe contains a plurality of fibers. The fiber optic probe may be moved longitudinally to a retracted position and at least one extended position outside of the endoscope.

Such a system enables access to parts of the body that current systems, such as bronchial endoscopes, cannot image due to their congestion. In fact, the systems according to embodiments of the invention each comprise a miniaturized fiber optic probe positioned inside the working channel of an endoscope. The cross-section of this fiber optic probe is smaller than that of the endoscope. The endoscope is inserted inside the body of a subject, as far as the section of the endoscope allows. Then, the fiber optic probe inside the working channel of the endoscope is moved longitudinally towards an imaging position, beyond the distal vision of the endoscope. This enables a system according to embodiments of the invention to image a part of the body of a subject that current systems are unable to access, and thus unable to image.

Preferably, the systems according to embodiments of the invention may include a mechanism to evaluate at least one position at the distal tip of the probe. Since the fiber optic probe may be moved longitudinally to a position of extension outside the endoscope, the distal tip of this probe is no longer visible via the endoscope. Thus, the position of the probe is no longer within the visual field of the endoscope. In this case, the operator has no control on the length of insertion of the probe, inside the lung, beyond the distal tip of the endoscope, which may present risks for the subject receiving the endoscope and the fiber optic probe. It then becomes important to track the position of the distal tip of the probe, in view of reducing risks of injury to the subject.

Mechanisms for tracking positions of the distal tip of the fiber optic probe may include at least a graduation on the optical probe, marked proximate the distal end of the optical probe, with this graduation visible to the eyes of an endoscopist to indicate a position of extension of the optical probe beyond the distal end of the endoscope. Thus, the operator is able to control the length of insertion of the distal tip of the optical probe. This graduation may be positioned at a known distance from the distal tip of the optical probe, depending on the body part that needs to be imaged. The tracking mechanism and method described above does not intend to exclude any other process or mechanism which could be used to locate the position of the distal tip of a probe inside a bronchial tree. For example, the tracking mechanism may use data obtained either in real time or using 3D modeling, adapted to the particular case of the subject under observation.

Preferably, at least one position of extension may be selected as the maximum extended position that should not be exceeded. This position of extension may be determined depending on performed images and the body part subjected to the imaging. This graduation (marker) may be set at a distance known from the distal tip of the fiber optic probe, depending on the body part subjected to the imaging.

Similarly, the at least one extended position may be selected as a position (or positions) at the onset of imaging, depending on the body part subjected to the imaging, and the actual imaging performed.

Preferably, the systems according to embodiments of the invention may be coupled with spectroscopic units for spectral analysis of the fluorescence signals captured by the fibers. The spectroscopic units supply spectral data concerning the fluorescence signals captured by the optic fiber probes. These spectral data may complement the imaging performed with information concerning the nature of the objects being imaged. Spectral analysis supplies information about the type of fluorescent molecule based on the detected signals (therefore about the type of tissue to which it is connected). In other cases, this analysis supplies information about the immediate surroundings of the fluorescent molecule (pH, enzyme activity, presence of lipids, presence of ions, etc.).

According to a particular embodiment of the invention, a fiber optic confocal fluorescence imaging system may otherwise comprise a hollow conduit inserted inside an endoscope, and fitted to receive a fiber optic probe, in such a way that it is possible to push the hollow conduit beyond the distal tip of the endoscope.

The hollow conduit, which acts as an intermediate catheter, and the fiber optic probe may advantageously cooperate to supply a suction piston effect at the distal tip of the hollow conduit, when said optic fiber probe retracts inside said hollow conduit.

According to another embodiment of the invention, an imaging process may be offered by an in vivo in situ fiber optic confocal fluorescence imaging system that comprises an endoscope equipped with a working channel for receiving a fiber optic imaging probe. Such a process may comprise the following steps:

Inserting the endoscope up to a distal obstruction. The obstruction is due to the relative diameters of the bronchi and the endoscope;

Inserting the probe in the alveolus, via extension outside of the working channel of the endoscope, until images of the alveoli is detectable (e.g., appear on a screen), and prior to reaching a known graduated distance on the probe.

A process according to embodiments of the invention Preferably enables imaging of an alveolus using a fiber optic probe, and thus, to obtain imageries of an area that the current processes are unable to supply.

A process according to embodiments of the invention may Preferably comprise tracking of a position of extension, corresponding to an initial imaging area. This position may correspond to the position from which the operator may expect to access the alveoli in need of imaging. Such tracking both facilitates and speeds the imaging process. In fact, insertion of the probe inside the alveolus may occur relatively swiftly up to this position, while taking care to avoid injury to the subject being imaged.

Preferably, a process according to embodiments of the invention may comprise tracking for a position of a maximum extension not to be exceeded, thus minimizing risks of injury to the subject being imaged due to overextension of the probe.

The positions of extension described below may depend on the imagery needed and the alveolus being imaged. They may depend on the relative distance of the distal tip of the probe compared to the distal tip of the endoscope. Within the context, for example, of the pulmonary alveolus of an adult male, tests showed that for a position corresponding to the initial imaging of the alveolus, the distal tip of the probe was located at a distance of about 2.5 cm from the distal tip of the endoscope. The maximum position of extension for this distance was 5.5 cm.

Thanks to this kind of tracking, a process according to embodiments of the invention can provide control of the position of the distal tip of the probe.

In a process according to one embodiment of the invention, the alveolus may be a human pulmonary alveolus of an adult or a child, under conditions of spontaneous or mechanical ventilation.

When a process according to embodiments of the invention is implemented in a fiber optic confocal fluorescence imaging system equipped with an intermediate catheter, it then additionally comprises an anchoring and visualization step, during which a hollow conduit, inserted inside a endoscope, is moved and functions as the working channel for a fiber optic probe, until the distal tip of the hollow conduit comes in contact with the biological tissue that needs to be examined, with the hollow conduit pushed beyond the distal tip of the endoscope.

This process may additionally include a suction phase of the biological tissue, following the anchoring and visualization step, during which the fiber optic probe is retracted inside the hollow conduit, thus supplying a suctioning piston effect at the distal tip of said hollow conduit.

Other advantages and characteristics of embodiments of the invention will become apparent in light of the detailed description of one or more of the embodiments, which are not intended to be limiting, and the appended drawings.

BRIEF DESCRIPTION OF THE DRAWINGS

FIG. 3 schematically represents a bronchial tree of a subject;

FIG. 4 is an image of an alveolus obtained with autofluorescence using a system according to one embodiment of the invention;

DETAILED DESCRIPTION

Figure 1:
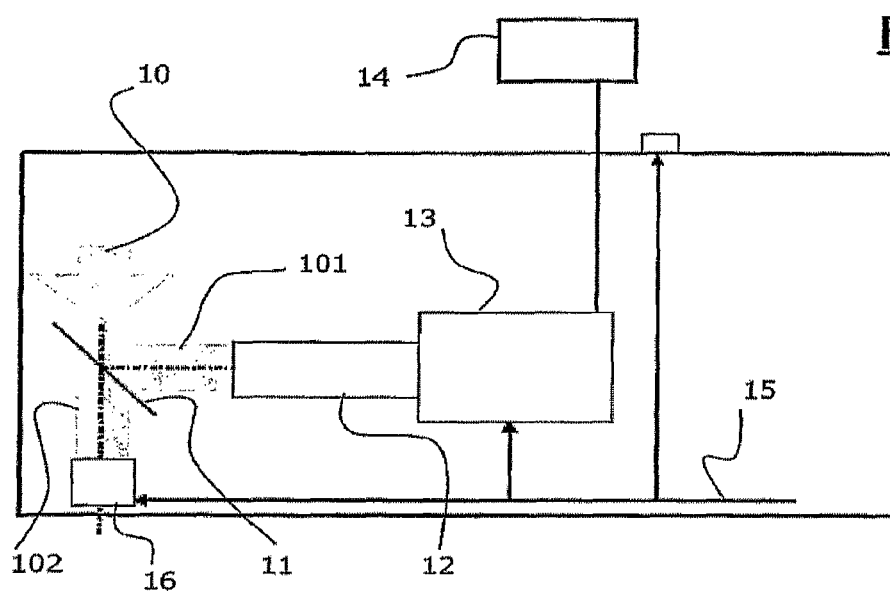
FIG. 1 schematically represents the use of a spectroscopic unit coupled to a system according to one embodiment of the invention.

A description now follows, in reference to the aforementioned figures, for examples of confocal fluorescence fiber optic imaging systems. In one example, a system according to embodiments of the invention comprises three main parts: an optoelectronic laser unit, a series of miniaturized probes comprising tens of thousands of optic fibers, and a software program for processing the images, for controlling the system, and or acquiring fluorescence signals captured by the fiber optic probe.

A laser source emitting a light having a wavelength around 488 nm scans in real time the proximal end surface of the optic fiber guide using scanning mirrors. Thus, the luminous excitation point is focused sequentially from fiber to fiber. This excitation signal carried to the distal tip of the optic fibers is then absorbed by the exogenous or endogenous fluorophores, depending on the case at hand with the probed tissue. These fluorophores respond with a signal at another wavelength (fluorescence emission wavelength), which is re-injected into the optic fibers of the image guide, following a reversed path. Each optic fiber filters light spatially, which is what supplies the fiber optic probe with high resolution imaging capacity. Once the return light is filtered, it is focused on a detector which enables electronic conversion of photons into a digital signal. Data is sent to the processor designed for processing, and generating images. This process preferably occurs in real time so that the operator constantly sees on screen what is being visualized during the complete tissue examination procedure.

Processing of the signals enables reconstruction of a tissue image using "raw" data corresponding to the light signals forwarded via the optic fibers. To obtain the most readable, and the most faithful image, compared to reality, the machine may require a two-step calibration process:

1. Measurements of the emissions of each fiber (autofluorescent or Raman diffusion) in view of subtracting these from the received signal, and 2. Calculation of the level of injection/transmission of each fiber, in view of homogenizing fiber response for the entire image guide.

Once calibration is performed, preferably in an automatic mode, a fiber optic confocal fluorescence imaging system according to embodiments of the invention is ready to be used. The operator will then see the images acquired in real time at a rate fast enough to give a real time (or near real time) image (e.g., 12 images per second) on a computer screen, preferably with accentuated contrast and all spatial distortions eliminated for better image quality.

For the example descried here, an imaging system according to embodiments of the invention may be used for in vivo bronchopulmonary imaging, and more particularly of the alveoli, benefiting from the autofluorescence properties of lungs, and thus of the endogenous fluorescent molecules of the lungs, and more particularly those of the alveoli. Thus, exogenous application of fluorescent reagents is un-necessary to capture fluorescence signals.

However, the fluorescence signal may be linked to the presence of various fluorescent molecules listed in the following table. Even though 488 nm is not the optimal excitation wavelength for these components, signals are nonetheless detectable from these various fluorescent molecules.

| Fluorescent Molecules | Approx. wavelength of absorption (nm.) | Max. wavelength of fluorescence (nm) | Source |
| --- | --- | --- | --- |
| Tryptophan | 275 | 350 | Protein |
| Collagen | 335 | 390 | Connective tissue |
| Elastin | 360 | 410 | Connective tissue |
| NADH | 340 | 470 | Respiratory channel |
| Flavin | 450 | 520 | Respiratory channel |
| Porphyrin | 405 | 635 | Bacterial infection, heme synthesis |

A single image, corresponding to a unique signal intensity per pixel, is not enough to supply information on the nature of the imaged components. The diverse components can however be discriminated via spectroscopy. FIG. 1 represents the use of a spectroscopic unit coupled to the system of the invention. The captured fluorescence signal 10 via an optic fiber is split into two fluorescence signals 101 and 102 by a beamsplitter 11. The fluorescence signal 102 is sent by the beamsplitter 11 to a detector 16, whereas the fluorescence signal 101 is sent towards a module 12, designed to collect signals sent by each of the optic fibers of the fiber optic probe. Collected optic signals are then sent to the spectroscopic unit 13, connected to a computer unit 14, comprising software controlling the spectroscopic unit 13. The spectroscopic unit brings (decodes) information about the nature of the fluorescent molecules, in addition to their location in space supplied by the image.

Acquisition of the image and spectra may be synchronous. A sequence of acquired images, in an imaged area, is completed with spectra acquired on the volume included in that which is used for imaging. Synchronization of the acquisition of images and spectra is obtained via a synchronization signal 15.

Figure 2:
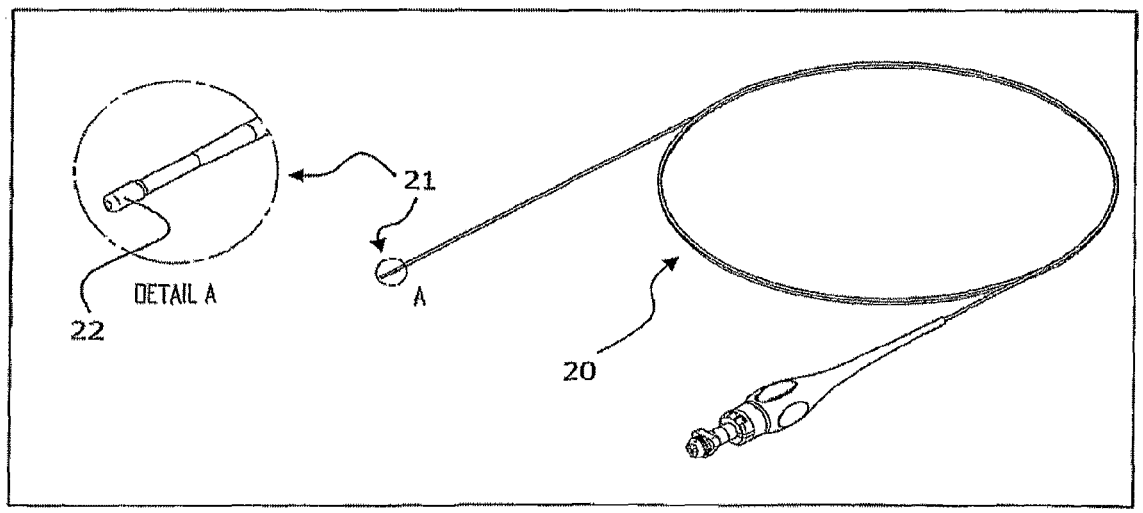
FIG. 2 schematically represents a fiber optic probe used in a system according to one embodiment of the invention.

For the example described here, an imaging system includes an endoscope, and in particular a bronchial endoscope, comprising a working channel with a cross-section measuring 2 mm in diameter. The probe that is used, and which is schematically represented in FIG. 2, is a fiber optic probe 20 of the type S with a diameter measuring 1.4 mm, and with no optic component at the distal tip 21. This probe 20 comprises, at the distal tip 21, a ferule 22, to ensure that the tip is impervious and non aggressive on tissue. Such a probe is inserted easily in the working channel of the bronchial endoscope, as it is compatible with the size of endoscopic channel operators, and non obstructive. The following Table summarizes the properties of this probe.

| Length | 3 m |
|---|---|
| Distal diameter | 1.4 mm |
| Diameter of the sheath | 1.4 mm |
| Length of the rigid part of the ferule | 3 mm |
| Lateral resolution | 3.5 μm |
| Visual field | 600 × 500 μm |

The respiratory system 30, represented in FIG. 3, is divided into two parts: one extending from the nose to the larynx 31, and the other consisting of the trachea 32, itself divided into two main bronchi, referred to as the primary bronchi 33, then in a dichotomous manner into numerous ramifications consisting of secondary bronchi 34, and tertiary bronchi 35, up to the respiratory bronchiole 26, and alveolar systems 37.

Following administration of local or general anesthesia to the subject, the bronchoscope is inserted into the trachea, and down the bronchial tree. The territory that is explored extends to the third or fourth subsegmental division. Only the bronchi may be visualized directly via the bronchial endoscope.

The smallest bronchoscope with a big enough working channel for insertion of the probe is used for imaging of the alveoli. Thus, it is possible to limit the distance of insertion of the probe beyond the endoscope, and consequently, to better ensure the safety of the patient. An endoscope with a diameter of 4.3 mm and a length of 60 cm was used for the endoalveolar exploration protocol. When the endoscope could not be inserted further due to diameter, a fiber optic probe 20 of the type S was pushed beyond the endoscope to the alveoli, while imaging the pathway with fiber optic confocal fluorescence, enabling progressive identification of the terminal bronchiolus, followed by the respiratory bronchioli via increasingly tightened concentric circles and finally the alveolar sacs.

Despite visualization of such a progression, when the probe exits from the endoscope and is pushed towards the alveoli, the distance of insertion of the probe should be known in view of avoiding the pleura, at the periphery of the lungs, representing a theoretical pneumothoracic risk of pleural perforation. To respond to this tracking problem, graduations were added to the design of the probe described previously. Experiments using cadavers validated the positions of both graduations: the first is located at 2.5 cm from the tip and the second at 5 cm. The area located between the graduations represents the alveolar sector, which is usually accessed, and which can be imaged.

When no images of an alveolus are obtained prior to the second graduation, the territory remains un-explored and the probe is removed. When the probe is in the alveolar territory, both dynamic sequence and spectra are recorded.

FIG. 4 represents an alveolus that was imaged via fluorescence using a system of the invention. On FIG. 4, there are several tissue planes visualized. However, as the diameter of an alveolus measures about 300 μm, the fiber optic probe is thus deemed to collect signals of at least up to 300 μm of the alveolar tissue. The system of the invention thus enables imaging of the content and of the walls of the alveolar sac, into which the fiber optic probe was inserted.

Figure 5:
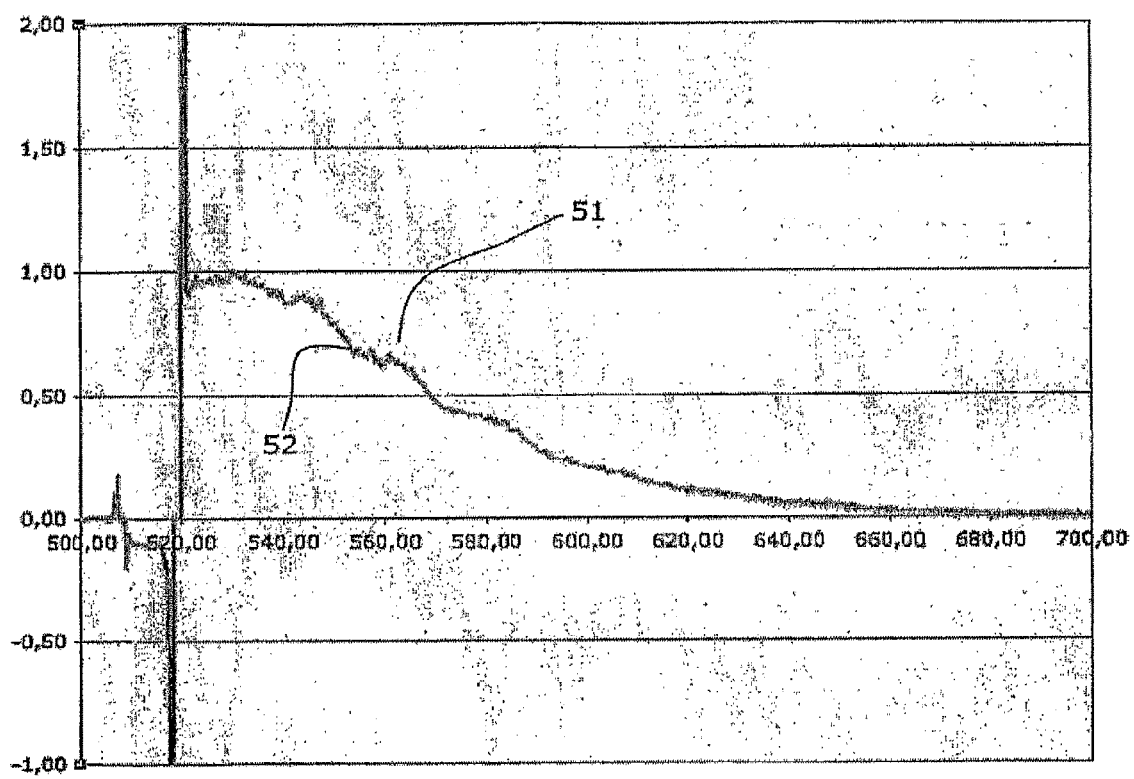
FIG. 5 represents spectra obtained with a spectroscopic unit coupled to a system according to one embodiment of the invention.

FIG. 5 represents spectrum 51 of fluorescence signals captured by the fiber optic probe. To be noted that both spectra are offset in terms of bandwidth, with this bias linked to instrumentation and applicable to both of the spectra. FIG. 5 also represents the pure elastin spectrum 52. Processing of the data output from the spectroscopic unit demonstrated that a major component of the fluorescence signal was linked to the presence of elastin. More fine tuned analysis is required to identify the contribution of other fluorescent molecules. It is well known that elastin is present in the walls of alveoli. Thus there is concordance between the type of object observed and localization of the fluorescent molecule.

Figure 6:
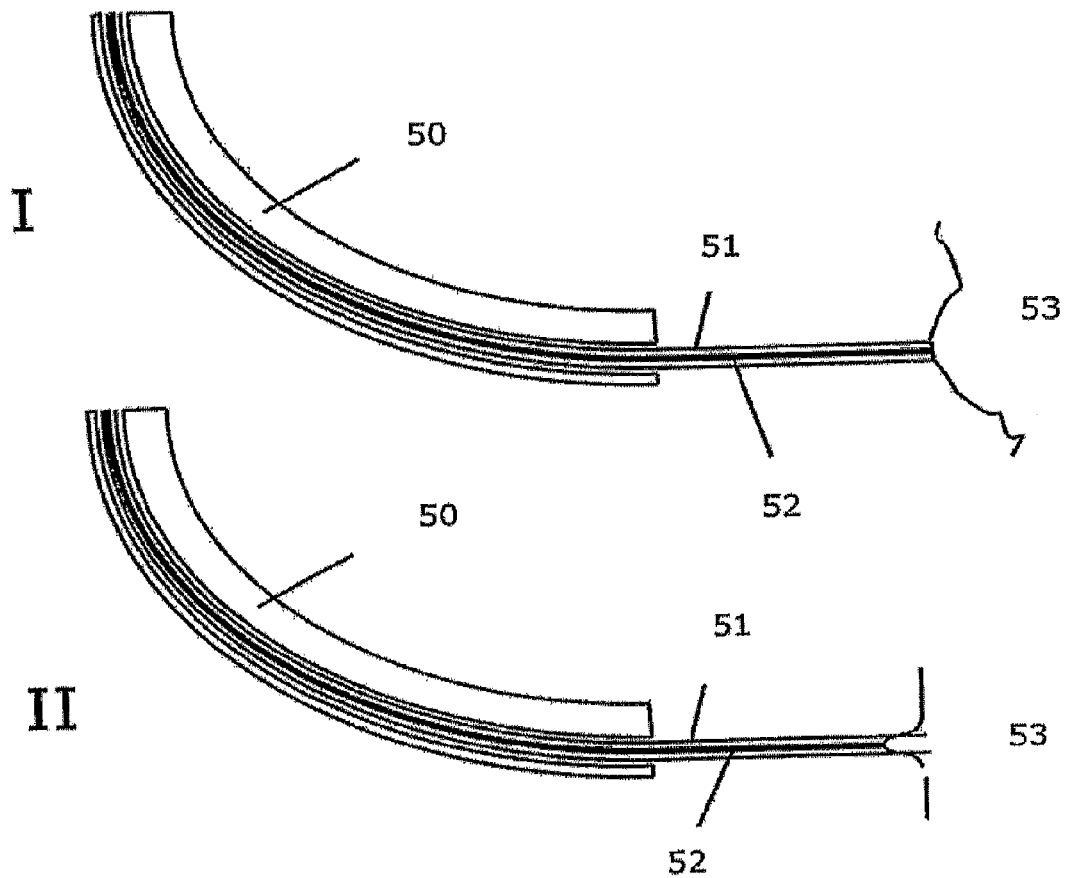
FIG. 6 illustrates a particular configuration of a fiber optic confocal imaging system according to one embodiment the invention.

A fiber optic confocal fluorescence imaging system according to embodiments of the invention may also be equipped with an intermediate catheter, as illustrated in FIG. 6.

In this configuration, a fiber optic probe 52 is placed inside a hollow conduit consisting of an intermediate catheter 51, itself inserted inside the endoscope 50. The intermediate catheter 51 then functions as a working channel for the fiber optic probe 52.

In an initial mode of use (I), the intermediate catheter 51 is moved from the working channel until it comes in contact with the biological tissue (53), which needs to be examined. The fiber optic probe 52, flush with the exit of the intermediate catheter 51, is then within immediate proximity, or in contact with the surface of the biological tissue 53, and visualization of this tissue is performed.

In a second mode of use (II), following visualization, the fiber optic probe 52 is retracted while the intermediate catheter is maintained against the biological tissue 53. Retraction yields a piston effect which enables suction of biological material from tissue 53, inside the intermediate catheter 51. This functionality thus enables easy sampling of the biological material directly at the visualization site.

To be noted that positioning of the intermediate catheter 51, against the biological tissue 53, may be performed using the tracking technique with graduations, as previously described, or even using techniques of three-dimensional representation of the anatomy of the body and the organs under examination, using current imaging processes and those of conventional tomography.

Of course, the invention is not limited to the examples described in the above, and numerous accommodations or modifications could be designed without exceeding the scope of the invention, such as for example the imaging of the distal bronchiole and its content, and the analysis of certain cells contained in distal pulmonary spaces that contain fluorescence properties.

The invention claimed is:

1. A method for imaging a tissue, comprising:
    collecting a light signal from at least part of said tissue, using a fiber optic probe for fluorescence imaging,
        wherein the fiber optic probe comprises a plurality of optic fibers contributing to said collecting of the light signal,
        wherein the plurality of optic fibers extends in a direction that is parallel to a longitudinal axis of the fiber optic probe;
    extending the fiber optic probe so that a distal tip of the fiber optic probe is placed at a distance of 15-300 micrometers from a target tissue to be imaged in the direction that is parallel to the longitudinal axis of the fiber optic probe, said imaging being made confocal at a proximal tip of said fiber optic probe; and obtaining a fluorescence image of the target tissue using the optical probe,
wherein a tracking mechanism is used in the extending step to guide the extension of the distal tip of the fiber optic probe, such that the distal tip of the fiber optic probe is placed at the distance of 15-300 micrometers from the target tissue for imaging of the target tissue.

2. The method according to claim 1, wherein the light signal consists of a fluorescence signal emitted by at least an exogenous fluorescent molecule.

3. The method according to claim 1, wherein the light signal comprises a fluorescence signal emitted by an endogenous fluorescent molecule.

4. The method according to claim 1, wherein the tissue is a tissue from a pulmonary alveolus.

5. The method according to claim 1, wherein the tissue is a tissue from a distal bronchiolus.

6. A fiber optic confocal fluorescence imaging system, comprising:
   an endoscope equipped with a working channel, in which a fiber optic probe has been inserted, wherein the fiber optic probe is movable longitudinally between a retracted position and at least one position of extension, in which a distal tip of the fiber optic probe is outside of the working channel;
   said fiber optic probe comprising a plurality of optic fibers for performing imaging of a target tissue at a distance of 15-300 micrometers from the target tissue, said imaging being confocal via a processor located at a proximal tip of said fiber optic probe, and
   a tracking mechanism that guides the extension of the distal tip of the fiber optic probe, such that the distal tip of the fiber optic probe is placed at the distance of 15-300 micrometers from the target tissue for imaging of the target tissue,
   wherein the plurality of optic fibers extends in a direction that is parallel to a longitudinal axis of the fiber optic probe, and
   wherein the position of extension places the distal tip of the fiber optic probe at the distance of 15-300 micrometers from the target tissue in the direction that is parallel to the longitudinal axis of the fiber optic probe.

7. The system according to claim 6, wherein the tracking mechanism comprises a graduation appended to the fiber optic probe proximate the distal tip, said graduation being visible with the endoscope, and indicating a position of extension.

8. The system according to claim 6, further comprising a tracking marker corresponding to a maximum position of extension which is not to be exceeded.

9. The system according to claim 6, further comprising a tracking marker corresponding to a position at the onset of visualization.

10. The system according to claim 6, wherein said system is configured to be coupled with a spectroscopic unit for performing spectral analysis of a fluorescence signal captured by at least one of the plurality of optic fibers.

11. The system according to claim 6, further comprising a hollow conduit, inserted inside the endoscope and fitted to receive the fiber optic probe, wherein said hollow conduit can be pushed beyond the distal tip of said endoscope.

12. The system according to claim 11, wherein the hollow conduit and the fiber optic probe are configured to cooperate to produce a piston suction effect at the distal tip of said hollow conduit, when said fiber optic probe is retracted inside said hollow conduit.

13. A method for imaging an alveolus, comprising:
   placing an endoscope into a respiratory tract of a subject;
   extending an optical probe, comprising a plurality of optical fibers, which is disposed inside a working channel of the endoscope, such that a distal tip of the optical probe extends beyond a distal end of the working channel,
      wherein the plurality of optical fibers extends in a direction that is parallel to a longitudinal axis of the optical probe,
      wherein extending the optical probe places the distal tip of the optical probe at a distance of 15-300 micrometers from the alveolus to be imaged in the direction that is parallel to the longitudinal axis of the optical probe, and does not put the distal tip of the optical probe in contact with the alveolus, and
   wherein a tracking mechanism is used in the extending step to guide the extension of the distal tip of the optical probe, such that the distal tip of the optical probe is placed at the distance of 15-300 micrometers from the alveolus to be imaged for imaging the alveolus; and
   obtaining a fluorescence image of the alveolus using the optical probe.

14. The method of claim 13, wherein the fluorescence image is a confocal image.

15. The method of claim 13, further comprising analyzing a fluorescence signal obtained with the optical probe to identify a molecule producing the fluorescence signal.

* * * * *